United States Patent [19]
Wallstén

[11] Patent Number: 4,990,151
[45] Date of Patent: Feb. 5, 1991

[54] DEVICE FOR TRANSLUMINAL IMPLANTATION OR EXTRACTION

[75] Inventor: Hans I. Wallstén, Villa Pré-Boisé, Sweden

[73] Assignee: Medinvent S.A., Lausanne, Switzerland

[21] Appl. No.: 408,362

[22] Filed: Sep. 18, 1989

[30] Foreign Application Priority Data

Sep. 28, 1988 [SE] Sweden .................. 8803444

[51] Int. Cl.$^5$ .................................... A61B 17/00
[52] U.S. Cl. ........................... 606/108; 606/198
[58] Field of Search ............ 606/108, 109, 206, 207, 606/210, 198, 191; 294/100

[56] References Cited

U.S. PATENT DOCUMENTS

| | | | |
|---|---|---|---|
| 611,038 | 9/1898 | Lohman | 606/207 X |
| 4,393,872 | 7/1983 | Reznik et al. | 606/206 X |
| 4,732,152 | 3/1988 | Wallstén et al. | 606/108 |
| 4,787,899 | 11/1988 | Lazarus | 606/108 X |

FOREIGN PATENT DOCUMENTS 1497799  1/1978  United Kingdom .

*Primary Examiner*—Michael H. Thaler
*Attorney, Agent, or Firm*—Burns, Doane Swecker & Mathis

[57] ABSTRACT

A device for transluminal implantation or extraction of a substantially tubular, radially selfexpanding stent (27), comprising a central tube (3) surrounded by an exterior tube (5) axially displaceable relative to the central tube (3), and a plurality of axially extending spring members (21) attached to the outer surface of said central tube (3) at the distal end thereof, said members being substantially evenly distributed around the periphery of said tube and capable of outward springing action of their front ends when retracting said exterior tube (5) from the distal end of said central tube (3).

19 Claims, 2 Drawing Sheets

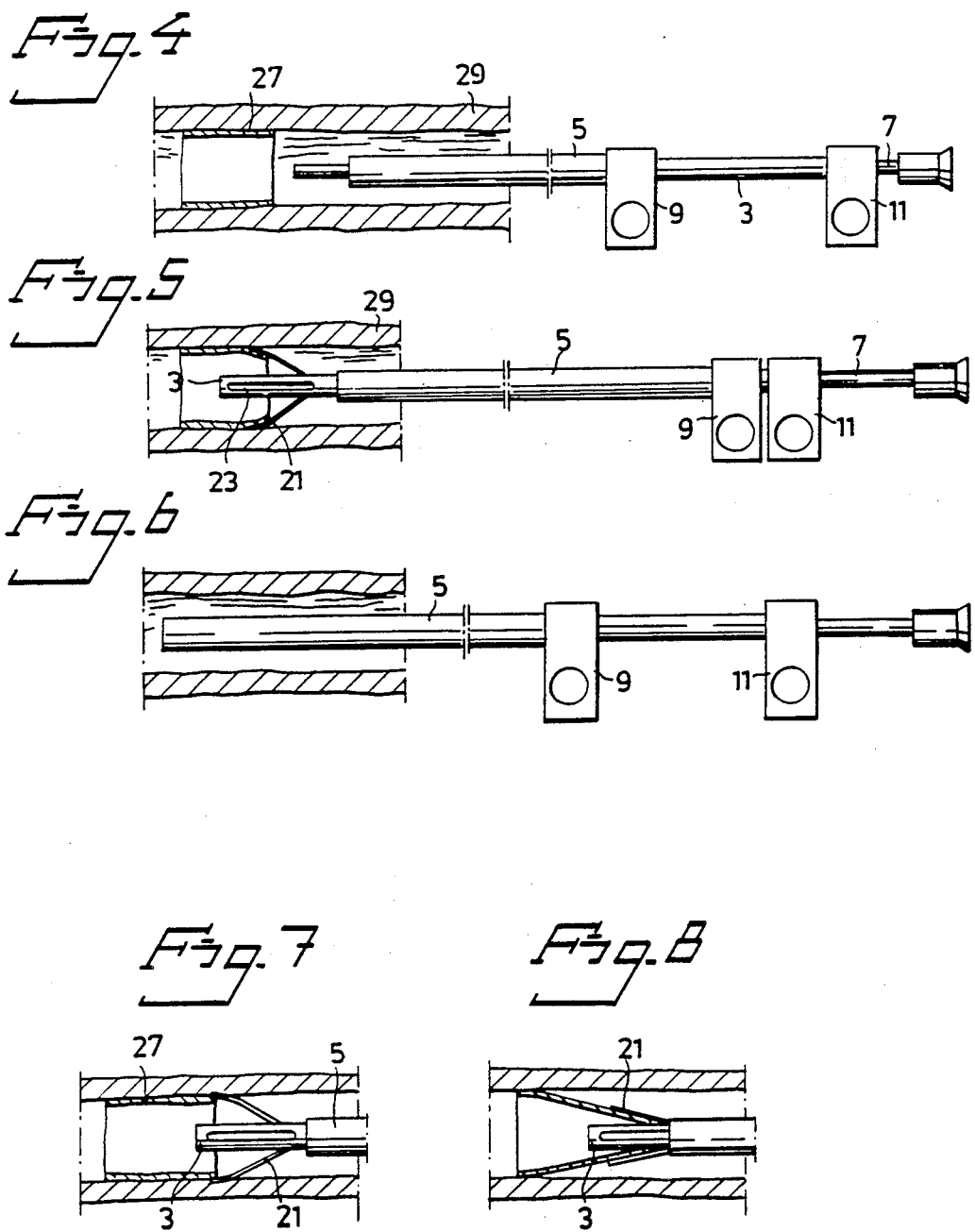

DEVICE FOR TRANSLUMINAL IMPLANTATION OR EXTRACTION

The present invention relates to a device for transluminal implantation and/or extraction of a substantially tubular, radially expanding stent.

Devices for transluminal implantation of expanding stents or prostheses are previously known. Thus, U.S. Pat. No. 4,732,152 describes a device enabling transluminal implantation of self-expanding stents. The device described in said U.S. patent shows excellent performance in regard to enabling implantation of prostheses or stents in, for example, blood vessels or other ducts in living animal bodies. However, most implantation devices including that described in U.S. Pat. No. 4,732,152 suffer from the serious drawback of not enabling later extraction of an implanted prosthesis or stent. Such extraction of the implanted artifact will sometimes be necessary due to improper location or disturbances created by the presence of the stent.

The present invention has for a main object to provide for an implantation device also enabling easy extraction of an implanted expanding stent when desired.

Another object of the invention is to provide for a device which can be used for implantation as well of a self-expanding stent.

Still another object of the invention is to provide a device enabling proper positioning of such self-expanding stent in connection with its implantation.

For these and other objects will be clear from the following description the invention provides for a device comprising a central tube surrounded by an exterior tube axially displaceable relative to the central tube, and a plurality of axially extending gripping members attached to the outer surface of said central tube at the distal end thereof, said members being substantially evenly distributed around the periphery of said tube and capable of outward expanding action of their front ends when retracting said exterior tube from the distal end of said central tube. Reversely, said gripping members are capable of forming a nip between themselves and the central tube when the exterior tube is moved forward in an axial direction towards the distal end of the central tube.

According to a modification of such device based on the same inventive concept, said exterior tube is provided with a backwardly extended end section at the distal end of said tube, and the plurality of axially gripping members are attached to the outer surface of said exterior tube at the distal end thereof. Again, said members are substantially evenly distributed around the periphery of said exterior tube and they are capable of outward expanding action at their rear ends when said exterior tube is retracted from the annular space formed by said extended end section and the part of the interior tube surrounded by said section. Reversely, when extracting a stent, said gripping members are capable of forming a nip between themselves and said exterior tube by moving the central tube backwardly in axial direction towards the proximal end of the exterior tube. The number or gripping members is at least three and a preferred number is four, although more than four gripping members can be used.

In a preferred embodiment of the device according to the invention, gripping handles are provided at the rear or proximal ends of said tubes, said means enabling axial relative movement between said tubes for expanding or folding of said spring members.

To enable proper positioning of the stent in connection with its implantation, the central tube may be provided with radial openings preferably at the distal end thereof, through which the site of implantation can be inspected for the purpose of finding the correct location for the stent. It is also possible to make the central tube, at least at the distal end thereof, of a transparent material enabling such inspection.

In the modification of the device according to the invention, both the central tube and the exterior tube may be provided with such radial openings at least at the distal ends thereof. Such radial openings are juxtaposed to enable proper inspection in connection with implantation. According to another embodiment said tubes are, at least at the distal ends thereof, made of transparent material to enable proper positioning. According to still another embodiment one of said tubes can be provided with radial openings at the distal end thereof, whereas the other tube can be made of a transparent material.

To enable inspection of the implantation site the device may comprise viewing means such as an endoscope or a telescope positioned inside the central tube and being axially displaceable therein.

To enable access to any location even through tortuous paths to the site of implantation the device according to the invention may be made of a flexible material including also said viewing means if present.

The invention also includes an apparatus for implanting an expandable stent, said apparatus comprising a device as defined above in combination with a stent which is positioned or clamped between said gripping members and said central tube in a contracted state. According to an alternative apparatus this combination is provided with the stent positioned or clamped between said gripping members and said exterior tube in a contracted state. In such apparatuses the stent is preferably of the self-expanding type, and it is particularly preferred to use stents of the type described in U.S. Pat. No. 4,655,771.

To facilitate the practical handling of the device of the present invention it is preferred to arrange means which prevent relative rotation between the two concentric tubes. Thus, in order to keep the preferred handles enabling axial relative movement of the concentric tubes, i.e. the central tube and the exterior tube, it is important that said handles are aligned under operation, which will be the case if said tubes are prevented from relative rotation. Such means may be constituted by members of the nut and groove type or other suitable arrangement conventional in the art to prevent such relative rotational movement.

The device according to the present invention is useful for implantation or extraction of any radially expanding stent, but it is particularly useful for handling stents of the type of self-expanding stents described in U.S. Pat. No. 4,655,771, the full disclosure of which is incorporated herein by reference. The advantage of applying the present invention to braided stents of the type disclosed in said U.S. patent primarily lies in the fact that when one end of such stent is subjected to radial compression at several points of its periphery the whole stent without retracting from its annular shape will contract inwardly from the location where the radial forces act. Thus, even if radial forces are applied from the outside to one end of such stent at three different positions evenly distributed around the periphery of the stent there will be no local deformations of the stent at or near said end but the stent will reduce its diameter uniformly and the radial contraction will be transmitted axially along the stent for a substantial part of its length.

The gripping members may have any shape in cross section but they could have a substantially rectangular cross section by having a blade-like shape. They may in one end be attached to the central tube or the exterior tube, respectively, in any suitable manner, such as by welding, riveting, soldering or the like. In a preferred embodiment the gripping members are made of a blade shaped spring material and are preformed so that when released from the surrounding exterior tube respectively backwardly extended end section they spring outwardly with their free ends.

BRIEF DESCRIPTION OF THE DRAWINGS

The invention will now be described by non-limiting examples with reference to the appended drawings, wherein:

FIGS. 4 to 8 illustrate the procedure for extracting a stent implanted in the urethra of a patient.

DETAILED DESCRIPTION OF A PREFERRED EMBODIMENT OF THE INVENTION

Figure 1:
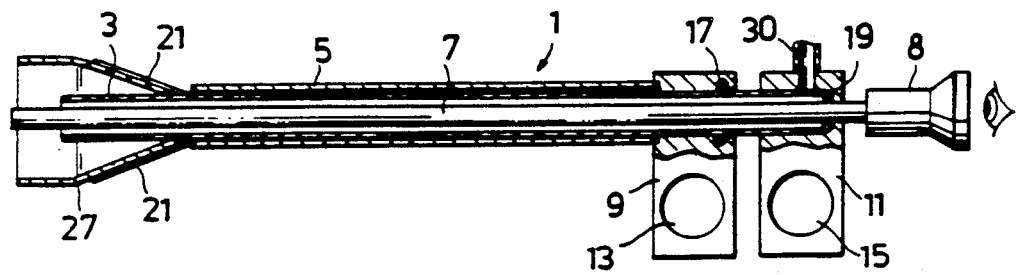
FIG. 1 is a diagrammatic side view, partly in section, of an embodiment of the device of the invention.

The device shown in FIG. 1 is generally designated 1 and is principally constituted by two flexible tubes, one central tube 3 and a surrounding exterior tube 5. Said tubes are substantially coextensive except for the fact that the exterior tube 5 is shorter than central tube 3 by a distance at least corresponding to the length of the stent to be implanted. Each of tubes 3, 5 is provided with gripping handles 9 and 11, respectively, attached at the rear ends thereof. Central tube 3 extends through handle 9 of the exterior tube for obvious reasons.

Figure 2:
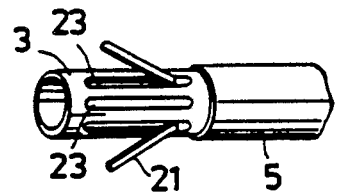
FIG. 2 is an enlarged detail of the distal end of the device shown in FIG. 1.

Central tube 3 is, at its distal end, provided with gripping members 21. The number of gripping members 21 is four and they are evenly distributed around the periphery of central tube 3. In the embodiment shown, gripping members 21 have a blade-like shape and can be made of a spring steel material. They can be attached to central tube 3 by any suitable means, such as welding, riveting or other way of attachment. In a preferred embodiment of the invention, members 21 are cut out of the wall of tube 3 as shown in FIG. 2 and are thus integral with the wall material of said tube. In such embodiment the tube material is suitably a metal or metal alloy having spring properties.

Gripping members 21 are capable of outward springing movement when exterior tube 5 is retracted by bringing handles 9, 11 together as shown in FIG. 1. When exterior tube 5 is moved axially forward along central tube 3 spring members 21 will fold and will come to close engagement with the exterior surface of central tube 3.

The device shown in FIG. 1 further comprises a viewing device in the form of a telescope 7 placed inside central tube 3 with its viewing end 8 positioned behind handle 11. For ease of operation handles 9, 11 are provided with cavities 13, 15 giving a steady grip.

As seen from FIG. 2 central tube 3 is provided with openings 23 suitably positioned for a purpose to be described below.

The device shown in FIG. 1 also includes seal rings 17, 19 sealing against the interior tube 3 and the telescope 7, respectively and inlet means 30, to allow a fluid such as water to be injected to the chamber between the telescope and the inner tube 3 allowing a stream of fluid to rinse the distal end of the telescope for better viewing.

Figure 3:
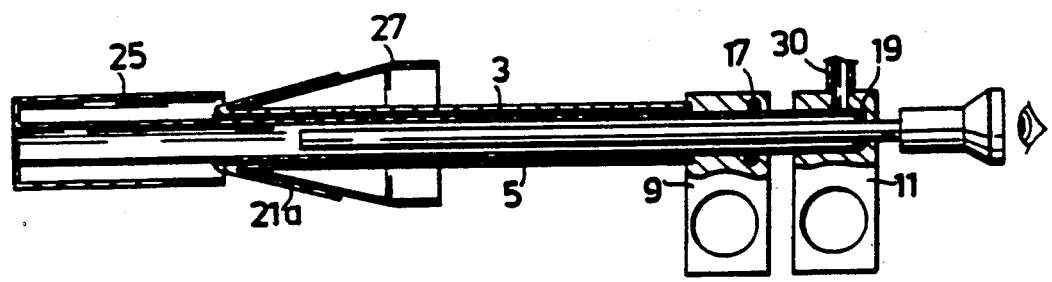
FIG. 3 is a diagrammatic side view of a modification of the instrument shown in FIG. 1 enabling release or extraction of a stent in the opposite direction.

The embodiment shown in FIG. 3 enables implantation and extraction of a stent from the opposite direction. In view of the construction of the stent, compression thereof results in axial extension. Therefore, one end of the stent when released will obtain an exact location in connection with its implantation, whereas its other end will be located in dependence on the ratio between radial contraction and axial expansion. Therefore, the embodiment of FIG. 3 may be useful when the rear end of the stent is to be correctly positioned in an exact location in a lumen.

The device shown in FIG. 3 corresponds in predominant parts to that shown in FIG. 1, but the distal end of central tube 3 is provided with an outwardly and backwardly bent end section 25. Moreover, the gripping members 21a are directed rearwardly and attached to the distal end of exterior tube 5 rather than directed forwardly and attached to central tube 3 as shown in FIG. 1. In other respects the device shown in FIG. 3 corresponds closely to that shown in FIG. 1.

In the embodiment shown in FIG. 1, for loading purposes, the proximal end of a stent 27 of the type described in U.S. Pat. No. 4,655,771 is accomodated beneath gripping members 21, whereafter exterior tube 5 will be axially moved forward so as to move gripping members 21 radially inwardly to compress the proximal end of the stent 27 and keep it firmly in place in a nip against the central tube 3. By further moving the exterior tube 5 axially forward the entire stent 27 will be compressed and kept inside the exterior tube 5. When the loaded device is then inserted into the lumen of a patient, such as into a patient's urethra, not shown in FIG. 1, the telescope 7 can be axially positioned and by viewing through it the insertion can be closely inspected for establishing the proper location where stent 27 is to be released. After reaching the correct location for the distal end of the stent exterior tube 5 is moved back by handle 9. In the position shown in FIG. 1 the proximal end of the stent 27 is released from the nip between the gripping members 22 and the central tube 3. By pulling the entire device slightly backwards in relation to the urethra the entire stent is released and by moving the exterior tube 5 forwardly the gripping members 21 will fold inwardly surrounded by the protecting exterior tube 5 and the device can then be removed from the lumen, such as the urethra with the stent completely surrounded by exterior tube 5.

With regard to the embodiment shown in FIG. 3 the procedure is similar but when releasing in this case the proximal end of the stent 27 will first expand at the desired position of the vessel (not shown in this figure) by moving the central tube 3 axially forward and, in the position shown in FIG. 3, the stent 27 is released from the nip between the gripping members 21a and the exterior tube 5. The entire device is then pushed forward in relation to the vessel lumen to completely release the stent 27, whereafter the central tube 3 is moved axially backward to the right as seen in FIG. 3 to fold gripping members 21a by the movement of end section 25 against the exterior tube 5 and thus protect the lumen from being affected by the spring members. The device can then be retracted as a whole from the lumen involved.

The procedure used for removing an implanted stent in the urethra 29 will now be described with reference to FIGS. 4 to 8.

FIG. 4 shows a stent implanted into a vessel 29 of a patient, e.g. the urethra. The device used from extracting the stent from its location within the urethra is of the type shown in FIG. 1. For extracting however, the exterior tube 5 is first kept in a forward position keeping the spring members 21 in a folded position surrounded by the distal end of the tube 5 thus protecting the lumen of the vessel when moving the device. The encoscope 7 is used for locating the exact position of stent 27 as seen in FIG. 4. After reaching a position somewhat behind stent 27 exterior tube 5 is now moved backwardly, whereby spring members 21 will be released to engage the inside surface of urethra 29 with the distal ends just behind the proximal end of the stent 27. Due to the pressure exerted by spring members 21 onto the interior wall of the lumen, the device can be pushed axially forwardly as seen in FIG. 5, whereby the spring members 21 can slide onto the outside of the proximal end of stent 27. By moving exterior tube 5 to the left spring members 21 will be folded inwardly thus causing contraction of the proximal end of the stent which will be firmly kept in the nip between the spring members and the central tube 3. Further movement of exterior tube 5 to the left will bring the entire stent 27 together with spring members 21 to a position within the protecting exterior tube 5 as illustrated in FIG. 6. The device can now be removed from the urethra of the patient together with stent 27 in its contracted state.

FIG. 7 and FIG. 8 show a detail of the device according to FIG. 4. When removing a self-expanding stent as described in U.S. Pat. No. 4,655,771, the spring members 21 have only to slide a very short distance, such as a few millimeters onto the interior wall of the lumen, as shown in FIG. 7. FIG. 8 shows how the end of this type of stent when contracted by the tip of the spring members will be elongated axially in direction towards the fixed ends of the spring members thus giving sufficient length of fixation in the nip between the spring members and the interior tube 3 without pushing the device forward. p Also the device of the type shown in FIG. 3 can in a corresponding manner be used as an extractor for implanted stents.

Even if the device is described in relation to the treatment of urethras it is very suitable for the treatment of many other conduits in the human body. The same devices with optical viewing devices can be successfully used for treatments of such vessels as urethra, the trachea, oesophagus and also some blood vessels.

It is to be noted that the invention is not limited to the embodiments described herein. Thus, any suitable materials can be used for different parts of the instrument. It is preferred to use flexible materials to reach difficultly accessible locations of different types of lumen in which case also the viewing devices can be exchanged to or combined with any appropriate imaging device such as X-Ray, ultrasound. Moreover, the invention is useful not only with regard to the type of stent described in U.S. Pat. No. 4,655,771, although an excellent performance is obtained in relation to such stent.

What is claimed is:

1. A device for transluminal implantation and extraction of a substantially tubular, radially expandable stent, comprising a central tube surrounded by a concentric exterior tube axially displaceable relative to the central tube, a plurality of axially extending gripping members attached to an outer surface of said central tube at a distal end thereof, said members being substantially evenly distributed around the periphery of said central tube and outwardly expandable when said exterior tube is axially displaced from the distal end of said central tube and toward a proximal end of said device, radial openings provided in said central tube to receive said gripping members therein, said members forming a nip between said members and said central tube when said exterior tube is moved in an axial direction toward the distal end of said central tube and away from said proximal end.

2. A device according to claim 1, further comprising handle means at the proximal end of said tubes for releasing and folding of said gripping members so as to permit relative axial movement between said tubes.

3. A device according to claim 2, wherein at least three gripping members are provided.

4. A device according to claim 1, wherein at least three gripping members are provided.

5. A device according to claim 1, wherein said central tube at least at the distal end thereof, is a transparent material so as to permit visual positioning of the stent.

6. A device accoring to claim 5, further comprising viewing means positioned inside the central tube and axially displaceable therein.

7. A device according to claim 1, further comprising viewing means positioned inside the central tube and axially displaceable therein.

8. A device according to claim 1, wherein the concentric tubes are flexible so as to enable bending of the device.

9. A device according to claim 1, wherein said gripping members are springing members to permit an outward springing action when said exterior tube is displaced axially of said central tube.

10. An apparatus for implanting a substantially tubular, radially expandable stent, comprising a device according to claim 1 in combination with said stent positioned between said gripping members and said central tube in a contracted state.

11. An apparatus according to claim 10, wherein said stent is a self-expanding stent.

12. A device for transluminal implantation and extraction of a substantially tubular, radially expandable stent, comprising a central tube surrounded by an exterior tube axially displaceable relative to the central tube, said central tube being provided with an extending end section at the distal end thereof, and a plurality of axially extending gripping members attached to an outer surface of said exterior tube at the distal end thereof, said members being substantially evenly distributed around the periphery of said exterior tube and outwardly expandable by moving the central tube and extending end section axially forwardly, said members extending toward a proximal end of said exterior tube, said members forming a nip between said members and said exterior tube when said central tube is moved in an axial direction toward the proximal end of said exterior tube.

13. A device according to claim 12, wherein one of said tubes is provided with radial openings at the distal end to receive said gripping members therein.

14. A device according to claim 12, wherein said tubes have radial, juxtaposed openings at the distal end to permit visual inspection of the implantation site of the stent.

15. A device according to claim 12, wherein said tubes at least at the distal end thereof, are transparent so as to permit visual positioning of the stent.

16. An apparatus for implanting a substantially tubular, radially expandable stent, comprising a device according to claim 12 in combination with said stent positioned between said gripping members and said exterior tube in a contracted state.

17. An apparatus according to claim 16, wherein said stent is a self-expanding stent.

18. A device accoring to claim 12, further comprising handle means at the proximal end of said tubes for releasing and folding of said gripping members so as to permit relative axial movement between said tubes.

19. A device according to claim 12, wherein at least three gripping members are provided.

* * * * *